(12) United States Patent
Ma

(10) Patent No.: US 10,168,316 B2
(45) Date of Patent: Jan. 1, 2019

(54) METHOD AND APPARATUS FOR MEASURING ENDOGENOUS CO CONCENTRATION IN ALVEOLAR AIR

(71) Applicant: Shenzhen Seekya Bio-Sci & Tech Co., Ltd., Shenzhen, Guangdong (CN)

(72) Inventor: Yongjian Ma, Guangdong (CN)

(73) Assignee: Shenzhen Seekya Bio-Sci & Tech Co., Ltd., Shenzhen (CN)

( * ) Notice: Subject to any disclaimer, the term of this patent is extended or adjusted under 35 U.S.C. 154(b) by 162 days.

(21) Appl. No.: 15/466,840

(22) Filed: Mar. 22, 2017

(65) Prior Publication Data

US 2017/0191984 A1 Jul. 6, 2017

Related U.S. Application Data

(63) Continuation of application No. PCT/CN2014/087224, filed on Sep. 23, 2014.

(51) Int. Cl.
| | |
|---|---|
| *G01N 33/497* | (2006.01) |
| *A61B 5/097* | (2006.01) |
| *A61B 5/00* | (2006.01) |
| *A61B 5/08* | (2006.01) |
| *G01N 27/00* | (2006.01) |
| *G01N 33/00* | (2006.01) |
| *A61B 5/083* | (2006.01) |

(52) U.S. Cl.
CPC ......... *G01N 33/497* (2013.01); *A61B 5/0075* (2013.01); *A61B 5/082* (2013.01); *A61B 5/0836* (2013.01); *A61B 5/097* (2013.01); *G01N 27/00* (2013.01); *G01N 33/0029* (2013.01)

(58) Field of Classification Search
CPC ....... A61B 5/082; A61B 5/0836; A61B 5/097; G01N 33/497; G01N 2033/4975
See application file for complete search history.

(56) References Cited

U.S. PATENT DOCUMENTS

| | | | |
|---|---|---|---|
| 6,248,078 B1* | 6/2001 | Risby | A61B 5/097 600/529 |
| 7,445,601 B2* | 11/2008 | Kline | A61B 5/417 600/529 |
| 8,074,646 B2* | 12/2011 | Daly | A61M 16/0045 128/204.18 |
| 9,789,133 B2* | 10/2017 | Wager | A61M 16/12 |

(Continued)

*Primary Examiner* — David A Rogers

(57) ABSTRACT

A method and apparatus for measuring endogenous CO concentration in exhaled alveolar air, comprises: proposing a method for injecting samples in small amounts, multiple times, intermittently, and establishing a CO concentration relationship between sample gas and gas in a measuring chamber; establishing a "concentration difference/electrical level difference" difference value fitting method, to obtain a fitted standard curve for a difference value between the sample gas and base gas; establishing an apparatus for measuring a CO concentration difference and a $CO_2$ concentration difference between sample gas and base gas; proposing a method for compensating a measurement value for endogenous CO in exhaled alveolar air. The problem that the amount of sample gas in a breath test is small, and cannot completely replace the gas originally inside the measuring chamber, is solved. The effect of electrical level zero drift and residual CO of unknown concentration in cleaning gas is eliminated.

14 Claims, 2 Drawing Sheets

(56) References Cited

U.S. PATENT DOCUMENTS

| | | | | |
|---|---|---|---|---|
| 2004/0210154 | A1* | 10/2004 | Kline | A61B 5/417 |
| | | | | 600/532 |
| 2009/0163825 | A1* | 6/2009 | Hirsh | A61B 5/082 |
| | | | | 600/532 |
| 2010/0081955 | A1* | 4/2010 | Wood, Jr. | A61B 5/097 |
| | | | | 600/532 |
| 2011/0208018 | A1* | 8/2011 | Kiani | A61B 5/0205 |
| | | | | 600/301 |
| 2012/0288951 | A1* | 11/2012 | Acharya | B82Y 30/00 |
| | | | | 436/113 |
| 2014/0238399 | A1* | 8/2014 | Daly | A61M 16/0045 |
| | | | | 128/204.23 |
| 2015/0122260 | A1* | 5/2015 | Daly | A61M 16/0045 |
| | | | | 128/204.23 |
| 2016/0033476 | A1* | 2/2016 | Blake | G01N 33/497 |
| | | | | 73/23.3 |
| 2016/0153964 | A1* | 6/2016 | Donnay | A61B 5/0833 |
| | | | | 600/326 |
| 2016/0256485 | A1* | 9/2016 | Wager | A61K 33/00 |
| 2017/0074857 | A1* | 3/2017 | Dennis | G01N 33/497 |
| 2017/0191984 | A1* | 7/2017 | Ma | A61B 5/0075 |

\* cited by examiner

METHOD AND APPARATUS FOR MEASURING ENDOGENOUS CO CONCENTRATION IN ALVEOLAR AIR

CROSS REFERENCE TO RELATED APPLICATIONS

The present application is a Continuation Application of PCT application No. PCT/CN2014/087224 filed on Sep. 23, 2014. All the above are hereby incorporated by reference.

TECHNICAL FIELD

The present application relates to medical diagnosis field, and more specifically, relates to a method and an apparatus for measuring endogenous CO concentration in alveolar air.

BACKGROUND

A special and important role of the mammalian hematopoietic system is to generate erythrocyte which delivers oxygen to the tissues of the animal. Lifespan determination of erythrocyte can be used for the differential diagnosis of anemia and other diseases, understanding the disease pathogenesis and determining the prognosis of treatment. Accordingly, the measurement of human erythrocyte lifespan is essential. The study has confirmed that the difference between the CO concentration of the exhaled alveolar air and the CO concentration in the base gas of the place where the sample gas of the exhaled alveolar air was taken can be used to estimate human erythrocyte lifespan. Common methods for measuring CO concentrations in air comprise non-dispersive infrared spectroscopy, gas chromatography, electrochemical methods, mercury replacement methods, etc. Among others, non-dispersive infrared spectroscopy and electrochemical methods, because of the need for large amount of gas samples, are not suitable for the CO concentration measurement of the human body breath. The amount of samples needed by gas chromatography is small, and the measurement accuracy can also satisfy with the determination of the low CO concentration in exhaled alveolar air for estimating erythrocyte lifespan. However, the operation and maintenance of the instrument are complex and expensive, so it is not suitable for clinical use. At the same time, the measured value of the existing equipment is about the CO concentration in the measuring chamber, and there is a certain deviation between this concentration and the CO concentration in exhaled alveolar air under normal conditions. The reason for this deviation is due to the mixing of the ambient air caused by the inconsistent operation during the exhaled alveolar air sampling and injecting. The existing methods and equipments cannot identify and eliminate the deviation.

SUMMARY

The present application provides a method and apparatus for measuring endogenous CO concentration in alveolar air, aiming at: a. solving the problem that the original gas in the measuring chamber cannot be totally replaced by the gas of either sample gas or base gas to be measured due to the too small amount of either sample gas or base gas in the breath test; b. eliminating the effect of the electrical level zero drift which is difficult to control on the measurement accuracy of low concentration CO; c. eliminating the effect of the unknown amount of residual CO in cleaning gas on the measurement of low concentration CO; d. compensating the deviation of the concentration measurement value measured by absorption spectroscopy with an open measuring chamber, which deviation is caused by the difference between the ambient temperature and pressure at the measurement time and the ambient temperature and the pressure at the calibration time; e. compensating the deviation between the measured value of CO concentration in the sample gas and the actual value of CO concentration in the exhaled alveolar air due to the mixing of the ambient gas caused by the inconsistent operation during the exhaled alveolar air sampling and/or injecting. The defects of the existing methods and equipments that they cannot identify and eliminate the deviation will be overcome.

According to one aspect, a method for measuring an endogenous CO concentration in alveolar air is provided, which comprising following steps:

S1. setting an injecting-sample-into-chamber mode for sample gas and base gas of a set of breath test samples in absorption spectroscopy; wherein the injecting-sample-into-chamber mode comprises injection times of the sample gas and the base gas, a volume of each injection, an interval between two successive injections;

S2. establishing a "concentration difference/electrical level difference" difference value fitted standard curve for the CO and the $CO_2$ respectively, by using standard sample gas and standard base gas with known concentrations of CO and $CO_2$;

S3. measuring electrical level number corresponding to the concentration of the sample gas and the base gas at a same temperature and pressure by a same apparatus and calculating an electrical level difference and obtaining a concentration difference of the CO and a concentration difference of the $CO_2$ based on the difference value fitted standard curve in S2;

S4. calculating a concentration M in a volume ratio (V/V) of the endogenous CO in the exhaled alveolar air according to following compensation formula:

$$M = \frac{X_S^{CO} - X_B^{CO}}{d},$$

$$\text{wherein, } d = \frac{X_S^{CO_2} - X_B^{CO_2}}{5\%}.$$

In the method for measuring the endogenous CO concentration in the alveolar air of the present application, in the step S1, the injecting-sample-into-chamber mode comprises per injection volume of 40 ml~400 ml, an injection speed of 10 ml/s~200 ml/s, 2-9 injection times of each sample gas and each base gas, and the interval between two successive injections of 12 s~48 s.

In the method for measuring the endogenous CO concentration in the alveolar air of the present application, the step S2 specifically comprises the following steps:

S201. preparing CO standard sample gas of different concentrations and one standard base gas;

S202. taking gas treated by CO catalyst and desiccant or other catalytic or drying processes as cleaning gas to clean measuring chamber until the measuring chamber is filled with the cleaning gas;

S203. according to the above injecting-sample-into-chamber mode, measuring electrical level numbers of the standard sample gas and the standard base gas respectively; according to the above electrical level numbers of the standard sample gas and the standard base gas, obtaining the electrical level difference between the standard sample gas and the standard base gas;

S204. according to the electrical level difference and the concentration difference between the standard sample gas and the standard base gas, fitting the "concentration difference/electrical level difference" difference value fitted standard curve with following expression:

$$X_S^{CO} - X_B^{CO} = A(D_S^{CO} - D_B^{CO}) + B;$$

wherein, A and B are fitted constants, $X_S^{CO}$ is the CO concentration in the sample gas, $X_B^{CO}$ is the CO concentration in the base gas, $D_S^{CO}$ is corresponding electrical level number of the CO concentration in the sample gas, $D_B^{CO}$ is corresponding electrical level number of the CO concentration in the base gas.

In the method for measuring the endogenous CO concentration in the alveolar air of the present application, the step S203 further comprises:

cleaning the measuring chamber by the cleaning gas until the measuring chamber is filled with the cleaning gas;

according to the injecting-sample-into-chamber mode, injecting the standard base gas into the measuring chamber to obtain and store the electrical level number of the standard base gas after final injection and balancing;

cleaning the measuring chamber by the cleaning gas until the measuring chamber is filled with the cleaning gas;

according to the injecting-sample-into-chamber mode, injecting a first standard sample gas into the measuring chamber to obtain and store the electrical level number of the first standard sample gas after final injection and balancing;

obtaining the electrical level difference between the first standard sample gas and the standard base gas according to the electrical level numbers of the first standard sample gas and the standard base gas;

cleaning the measuring chamber by the cleaning gas until the measuring chamber is filled with the cleaning gas;

according to the injecting-sample-into-chamber mode, injecting the standard base gas into the measuring chamber to obtain and store the electrical level number of the standard base gas after final injection and balancing;

cleaning the measuring chamber by the cleaning gas until the measuring chamber is filled with the cleaning gas;

according to the injecting-sample-into-chamber mode, injecting a second standard sample gas into the measuring chamber to obtain and store the electrical level number of the second standard sample gas after final injection and balancing;

obtaining the electrical level difference between the second standard sample gas and the standard base gas according to the electrical level numbers of the second standard sample gas and the standard base gas;

repeating the above procedure to obtain a group of "concentration difference/electrical level difference" data pairs of a group of the standard sample gas and the standard base gas pairs.

In the method for measuring the endogenous CO concentration in the alveolar air of the present application, in the step S3, when measuring the concentration difference between the sample gas and the base gas in a set of breath test samples, its injecting order is the same as that of the standard sample gas and the standard base gas when fitting the difference value fitted standard curve.

In the method for measuring the endogenous CO concentration in the alveolar air of the present application, before measuring the CO gas in the sample gas and the base gas, water vapor and $CO_2$ gas are removed from the sample gas and the base gas.

According to a further aspect, an apparatus for measuring an endogenous CO concentration in alveolar air which is capable of measuring both CO concentration and $CO_2$ concentration, is also provided. The apparatus for measuring an endogenous CO concentration in exhaled alveolar air operates on a measuring principle of absorption spectroscopy with an open measuring chamber, and comprises:

a $CO_2$ gas measuring chamber and a CO gas measuring chamber, wherein the $CO_2$ gas measuring chamber and the CO gas measuring chamber are connected with a gas inlet through a tracheal line; wherein concentration of $CO_2$ gas $X_S^{CO_2}$, $X_B^{CO_2}$ or concentration difference of $CO_2$ gas $(X_S^{CO_2} - X_B^{CO_2})$ in sample gas and base gas, as well as concentration of CO $X_S^{CO}$, $X_B^{CO}$ concentration difference of CO gas $(X_S^{CO} - X_B^{CO})$ in the sample gas and the base gas are measured under a same temperature and pressure;

a processing unit, used for calculating a concentration net value M in volume ratio (V/V) of the endogenous CO in the exhaled alveolar air according to following compensation formula:

$$M = \frac{X_S^{CO} - X_B^{CO}}{d},$$

$$\text{wherein, } d = \frac{X_S^{CO_2} - X_B^{CO_2}}{5\%}.$$

The apparatus for measuring the endogenous CO concentration in the alveolar air of the present application, further comprises an injecting-sample-into-chamber system comprising the gas inlet, a gas pump, a general solenoid valve, a measuring chamber and an exhaust port; wherein the gas inlet is connected with the gas pump which is further connected with the measuring chamber through the general solenoid valve, the exhaust port is disposed on the measuring chamber which is communicated with external environment through the exhaust port; wherein, the injecting-sample-into-chamber system further comprises a gas control unit, a gas pipe and a cylinder; the gas control unit comprises a gas passage switching buffer, a sample gas solenoid valve, a base gas solenoid valve and a gas pump solenoid valve; wherein the gas passage switching buffer is connected between the gas pipe and the general solenoid valve; the sample gas solenoid valve, the base gas solenoid valve and the gas pump solenoid valve are all connected into the gas passage switching buffer; the sample gas solenoid valve and the base gas solenoid valve are respectively used for delivering the sample gas and the base gas to the gas passage switching buffer; the gas pump solenoid valve connected with the gas pump is used for delivering cleaning gas to the gas passage switching buffer; the cylinder connected with the gas pipe is used for injecting either the sample gas or the base gas to be measured into the measuring chamber through the gas pipe.

In the apparatus for measuring the endogenous CO concentration in the alveolar air of the present application, the gas control unit further comprises a spare solenoid valve for replacing the sample gas solenoid valve, the base gas solenoid valve or the gas pump solenoid valve.

In the apparatus for measuring the endogenous CO concentration in the alveolar air of the present application, the injecting-sample-into-chamber system further comprises a driving unit connected with a piston of the cylinder; wherein the driving unit comprises a base, a rotating screw rod and a stepping motor which are fixed on the base, and a slider which is disposed on the rotating screw rod and connected with the cylinder; the stepping motor drives the rotating screw rod to rotate so as to drive the piston to move, and inject either the sample gas or the base gas to be measured into the measuring chamber through the gas pipe.

The following advantageous effects can be obtained by implementing the present application.

(1) The injecting-sample-into-chamber mode of small volumes, multiple times and intermittent injecting is adopted to replace the approach that the original gas in the measuring chamber is totally replaced by the gas to be measured, this injecting-sample-into-chamber mode establishes a fixed relationship between the CO concentration of the gas in the measuring chamber and the CO concentration of the gas to be measured. Thus the required amount of the gas sample to be measured is reduced, and the problem that the original gas in the measuring chamber cannot be replaced totally by the-gas to be measured due to the small amount of either the sample gas or the base gas in breath test is solved.

(2) The sample gas and the base gas are measured in pairs and next to each other in time, and a "concentration difference/electrical level difference" difference value fitted standard curve for the pairs of the sample gas and the base gas is established. In such a way, the concentration difference between the sample gas and the base gas is obtained by measuring the electrical level difference between the sample gas and the base gas, then the effects of electrical level zero drift and unknown concentration of residual CO in cleaning gas on the endogenous CO concentration measurement of exhaled alveolar air is effectively eliminated, thus the measurement accuracy is effectively improved.

(3) The $CO_2$ concentration difference and the CO concentration difference in the sample gas and the base gas are measured respectively, and then the measurement values of the CO concentration difference in the sample gas and the base gas are compensated and corrected by a relatively stable $CO_2$ concentration in exhaled alveolar air. With the proportional concentrate or dilute relationship between the $CO_2$ concentration and CO concentration, this compensating method can be used to eliminate the deviation of the measured value due to the mixing of the ambient air caused by the inconsistent operation during the exhaled alveolar air sampling and injecting.

(4) When using the compensation formula of the endogenous CO measurement value of exhaled alveolar air to calculate the concentration net value M in volume ratio (V/V) of the endogenous CO in the exhaled alveolar air, the effect caused by the difference between the temperatures and pressures at the measurement time and the calibration time on the endogenous CO concentration measurement value in exhaled alveolar air will be eliminated.

BRIEF DESCRIPTION OF THE DRAWINGS

The present application will now be further described with reference to the accompanying drawings and the accompanying drawings.

DETAILED DESCRIPTION OF THE PREFERRED EMBODIMENT

Figure 1:
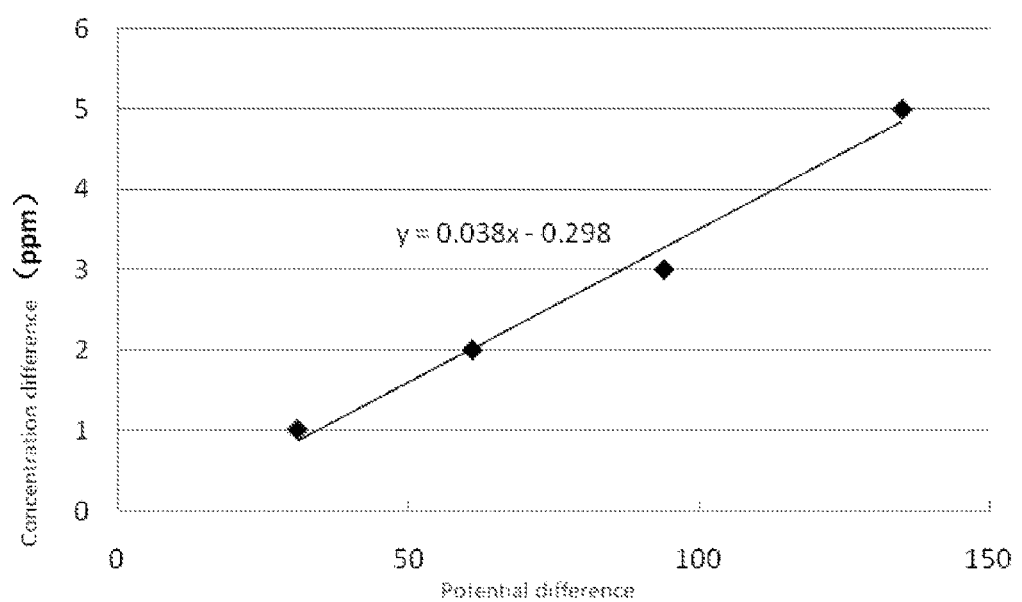
FIG. 1 is a "concentration difference/electrical level difference" fitted standard curve for measuring the CO concentration difference, according to a preferred embodiment of the present application.

For a clear understanding of the technical features, objects and effects of the present application, specific embodiments of the present application will now be described in detail with reference to the accompanying drawings.

When the CO concentration is measured based on the existing gas absorption spectroscopy technique, the following problems are faced. a. A large amount of the gas sample is needed for replacing the gas in the measuring chamber by the gas sample to be measured. b. When the CO concentration is low, it is difficult to control the electrical level zero drift which would influence the CO measurement a lot. c. The unknown residue CO concentration in the cleaning gas for cleaning the measuring chamber has an effect on the measurement accuracy on the CO concentration of the sample to be measured. d. The difference between the temperatures and pressures at the measurement time and the calibration time has an effect on the measurement result. e. When measuring the CO concentration in the exhaled alveolar air, the following problems are confronted. Only the CO concentration of the sample gas is measured, which is not equal to the CO concentration of the exhaled alveolar air. The prior art cannot identify and eliminate the deviation of the measured value of CO concentration in the sample gas and the actual value in the exhaled alveolar air due to the mixing of the ambient gas caused by the inconsistent operation during the exhaled alveolar gas sampling and injecting. For example, the longtime of holding breath leads to the CO concentration higher than that under normal circumstances, or the CO is diluted by the ambient air due to the bad seal during the gas generation or injecting.

The main innovation points of the present application are listed as follows. Firstly, an injecting-sample-into-chamber mode of small volumes, multiple times and intermittent injecting is adopted for the absorption spectroscopy, such that the right amount of the sample volume, the right injection speed, the right injection times, the right interval between two successive injections are chosen, and the sample to be measured are injected into the measuring chamber to establish a fixed relationship between the CO concentration in the measuring chamber after the injection and the CO concentration of the sample to be measured. Thus the amount of the sample gas is reduced and the problem that the sample gas in a breath test cannot completely replace the gas originally inside the measuring chamber is solved. Secondly, the difference value fitting method is adopted to establish a "concentration difference/electrical level difference" difference value fitted standard curve between the difference values in the sample gas, rather than a common "concentration/electrical level" fitted standard curve, that is a "concentration difference/electrical level difference" difference value fitted standard curve $X_S - X_B = A(D_S - D_B) + B$ for the CO standard sample gas, the $CO_2$ standard sample gas, the CO standard base gas and the $CO_2$ standard base gas is established. When the sample is measured, the same apparatus is employed for measuring the sample gas and base gas in pairs and next to each other in time to obtain the electrical level numbers of the sample gas and the base gas, and the electrical level difference $(D_S - D_B)$ therebetween. Then concentration difference between the sample gas and the base gas can be obtained according to the above "concentration difference/electrical level difference" difference value fitted standard curve $X_S - X_B = A(D_S - D_B) + B$. Such innovation effectively eliminates the effects of electrical level zero drift and residual CO of unknown concentration in cleaning gas on the endogenous CO concentration measurement in exhaled alveolar air, and effectively improves the measurement accuracy (for $CO_2$, since the $CO_2$ concentration of the exhaled alveolar air is much higher than that of the base gas, compared with the $CO_2$ concentration of the exhaled alveolar air, the $CO_2$ concentration of the base gas can be ignored). Thirdly, an apparatus which can be used for both the CO and the $CO_2$ measurement is constructed, which makes it easy to calculate the compensation and correction of the CO concentration with the $CO_2$ concentration. Fourthly, the measurement value of the $CO_2$ concentration is used to calculate and compensate the endogenous CO concentration in exhaled alveolar air, that is a $CO_2$ concentration difference and a CO concentration difference between the sample gas and the base gas are measured under the same pressure and temperature, then the endogenous CO concentration in exhaled alveolar air is calculated, compensated and corrected by the relatively stable $CO_2$ concentration in exhaled alveolar air according to the compensation formula. This innovation eliminates the deviation of the measured value due to the mixing of the ambient gas caused by the inconsistent operation during the exhaled alveolar gas sampling and injecting, and eliminates the effect on the measurement value of the sample caused by the difference between the ambient temperatures and pressures at the measurement time and the calibration time, thus obtaining a more accurate endogenous CO concentration in exhaled alveolar air.

Part One: Establishing a Difference Value Fitting Method

The problem that the amount of gas sample in a breath test is too small to completely replace the gas originally inside the measuring chamber, is solved through adopting the injecting-sample-into-chamber mode of small volumes, multiple times and intermittent injecting (the "gas sample" comprises "sample gas" and "base gas", wherein the "sample gas" is "the exhaled gas of the collected subject", the "base gas" is "the ambient gas where the exhaled gas is collected", the "sample", the "sample gas" and the "base gas" described in the text are the same), and specific principles are as follows.

Each sample to be measured is divided into multiple parts with small volumes for injection in multiple times. An interval is set between two adjacent injections to make sure the newly sampled sample gas and the gas retained in the measuring chamber are mixed evenly. To be more specific, (1) the movement speed and the gas intake amount of the cylinder piston are controlled to make sure that the gas exhausted from the exhaust port every time when the air is intake is the gas originally in the measuring chamber. That is the newly injection gas sample has not been exhausted, thus each sample volume and injection speed should be controlled in a range according to the volume of the measuring chamber, for example, the sample volume is 40~400 ml for each time and the injection speed is 10 ml/s~200 ml/s for each time; (2) the intermittent time between two adjacent injections (the interval between two adjacent injections) is controlled to make sure that the newly sampled gas sample and the unexhausted part of the gas originally in the measuring chamber are mixed evenly, for example, the interval between two injections is 12~48 s; (3) the injection times of each sample to be measured are controlled to make sure that the CO concentration of the newly sampled sample gas has enough influence on the CO concentration of the gas in the measuring chamber after the completion of multiple injections; that is each time the amount of intake gas cannot be too small, so that the impact of the new gas on the electrical level would not be too small to be detected with any changes; for example each sample to be measured is divided into 2~9 parts and a fixed relationship between the CO concentration of the gas in the measuring chamber after the sampling and the CO concentration of the sample to be measured is established.

In this embodiment, the concentration of the gas sample to be measured is set to be X, and the cleaning gas concentration is Y. Each gas sample to be measured is divided to 5 parts of 200 ml for injection, and the interval between two adjacent injections is 19 s, and the total volume of the measuring chamber measured by infrared spectrometer is 700 ml. After each injection and balancing, the CO concentration to be measured in the measuring chamber is as follows.

The CO concentration to be measured in the measuring chamber after the first injection and balancing is $$p_1 = \frac{2X}{7} + \frac{5Y}{7}. \quad (1)$$

The CO concentration to be measured in the measuring chamber after the second injection and balancing is $$p_2 = \frac{2X}{7} + \frac{5}{7}P_1 = \frac{24X}{49} + \frac{25Y}{49}. \quad (2)$$

The CO concentration to be measured in the measuring chamber after the third injection and balancing is $$p_3 = \frac{2X}{7} + \frac{5}{7}P_2 = \frac{218X}{343} + \frac{125Y}{343}. \quad (3)$$

The CO concentration to be measured in the measuring chamber after the fourth injection and balancing is $$p_4 = \frac{2X}{7} + \frac{5}{7}P_3 = \frac{1776X}{343} + \frac{625Y}{343}. \quad (4)$$

The CO concentration to be measured in the measuring chamber after the fifth injection and balancing is $$p_5 = \frac{2X}{7} + \frac{5}{7}P_4 = \frac{13682X}{16807} + \frac{3125Y}{16807}. \quad (5)$$

We can see from the formula (1)-(5) that, when the CO concentration Y of the cleaning gas is a constant, there is a linear relationship between the concentration $P_5$ of the gas to be measured in the measuring chamber after 5 times of injection and the concentration X of the injected gas sample to be measured. In this way, the volume of the gas sample needed by 5 injections is only 1000 ml. If the injection times are reduced, the volume of the gas sample to be measured will be less. Therefore, the problem that the gas in the measuring chamber should be completely replaced by the sample in the process of continuous injection is overcome.

In the present application, the cleaning gas is firstly used to clean the measuring chamber until the measuring chamber is filled with the cleaning gas. And based on the completion of cleaning, the injecting-sample-into-chamber mode of small volumes, multiple times and intermittent injection is adopted such that the right amount of the sample volume, the right injection speed, the right injection times, the right interval between two successive injections are chosen, and the sample to be measured are injected into the measuring chamber to establish a fixed relationship between the CO concentration in the measuring chamber after the injection and the CO concentration of the sample to be measured. Then the CO standard sample gas and standard base gas of known concentration and the $CO_2$ standard sample gas and standard base gas of known concentration are used to establish the "concentration difference/electrical level difference" difference value fitted standard curve for the CO and $CO_2$ respectively.

The first purpose of the present application is to measure the difference between the CO concentration in the sample gas and the CO concentration of the base gas of the location where the subject is located before the sample gas is taken. In general, the relationship between the signal level D and the CO concentration P in the measuring chamber is as follow:

$$D = K_0 P + D_0 \qquad (6)$$

Wherein $K_0$ refers to the slope and is a constant; $D_0$ is the electrical level when the CO concentration is zero (referred to as "electrical level zero"). The expression of the CO concentration in the measuring chamber in formula (5) is substituted into the formula (6) to obtain:

$$D = K_0 P_5 + D_0 = K_0 \left( \frac{13682 X}{16807} + \frac{3125 Y}{16807} \right) + D_0 = K_0' X + D_0' \qquad (7)$$

Wherein $K_0' = K_0 \frac{13682}{16807}$, $D_0' = D_0 + K_0 \frac{3125 Y}{16807}$.

A general standard curve is established by injecting a series of standard gas of known concentration into the measuring chamber to obtain the $K_0'$ and $D_0'$. When measuring the gas sample of unknown concentration, once the signal level D of the gas sample to be measured is measured, the concentration X of the sample to be measured can be calculated. However, it is difficult to realize on the electronics that the electrical level zero $D_0$ is the same at each boot or never drifts after a long boot time. Meanwhile, although before cleaning the measuring chamber the cleaning gas has been treated by catalyzing CO to $CO_2$, however a small amount of CO may not been completely cleaned from the cleaning gas, and the CO concentration in the cleaning gas is unknown. The uncertainty of $D_0$, Y leads to the uncertainty of $D_0'$. Therefore, the CO concentration in the sample to be measured cannot be accurately measured.

To overcome the uncertainty of $D_0$ and the unknown concentration Y of the CO residual in the cleaning gas, the present application adopts a method to measure the sample gas to be measured and the base gas in pairs and next to each other in time. Although the CO concentration Y in the cleaning gas is unknown and the signal levels of the corresponding concentration of the sample gas to be measured and the base gas are affected by Y, however as long as the sample gas to be measured and the base gas are measured next to each other in time, the CO concentration Y of the cleaning gas corresponding to the two measurements are thought to be the same and $D_0$ is almost unchanged in two measurements next to each other in time. So when the measurements of the sample gas to be measured and the base gas are next to each other in time, the effects of Y on the signal levels of the sample gas to be measured and the base gas can be considered as the same. When calculating the difference between the electrical level of the sample gas to be measured and the electrical level of the base gas, the effect of Y can be eliminated, and meanwhile when the concentration is zero, the drift effect of the electrical level zero $D_0$ on the electrical level difference (the electrical level difference between the sample gas to be measured and the base gas) is also substantially eliminated (as the measurements are next to each other in time, the drift of $D_0$ is small). That is $$D_S - D_B = K_0'(X_S - X_B) + (D_{0S}' - D_{0B}') \qquad (8)$$

In the same measurement period, as long as Y is kept unchanged (that is the concentration of the cleaning gas is unchanged), the drift of the electrical level zero $D_0$ can be ignored (because the two measurements are close to each other in time). Then, $(D_{0S}' - D_{0B}') \approx 0$, and the relationship between the $(D_S - D_B)$ and the $(X_S - X_B)$ is linear and approximately passes through the origin. That is, the measurement about the concentration difference between the sample gas and the base gas, in theory, is irrelevant to the concentration Y of the cleaning gas.

The formula (8) is further rewritten as:

$$X_S - X_B = A(D_S - D_B) + B \qquad (9)$$

When using the "concentration difference/electrical level difference" difference value fitted method, the lower limit of the CO concentration in sample gas is 0.05 ppm. The CO concentration corresponding to the human normal erythrocyte lifespan is 1.5 ppm. Thus, the sensitivity requirements for erythrocyte life measurement are satisfied.

Part Two, Experimental Verification of the Difference Value Fitting Method

Establishing a Difference Value Fitted Standard Curve

Firstly, the injecting-sample-into-chamber order and the injecting-sample-into-chamber mode of the sample gas and the base gas are set. The injecting-sample-into-chamber mode of small volumes, multiple times and intermittent injecting according to the present application is adopted. The sample volume and the injection speed of each injection and the injection times should meet the following requirements that the sampled sample gas will not be exhausted from the outlet of the CO measuring chamber and only the same volume of gas which is originally in the CO measuring chamber is exhausted; the length of the intermittent time between two adjacent injections should be sufficient to allow the injected sample gas to be mixed with the unexhausted portion of the original gas in the CO measuring chamber sufficiently. In this embodiment, each sample gas to be measured and the standard base gas are divided into 5 parts of 200 ml for injection, and the interval between two adjacent injections is 19 s. The injecting-sample-into-chamber order is that the standard base gas is measured at first and then the standard sample gas is measured. CO standard sample gas of different concentrations and one standard base gas are prepared. In this embodiment, the concentration of the CO standard sample gas is prepared to be 1 ppm, 2 ppm, 3 ppm, 5 ppm. The ultra-pure nitrogen which is catalyzed and with a low residual CO concentration ($\approx 0$ ppm) is prepared as the standard base gas.

The bags filled with CO standard sample gas with concentrations of 1 ppm, 2 ppm, 3 ppm, 5 ppm are respectively inserted in to the sample gas inlet of the apparatus, and the standard base gas is injected into the base gas inlet.

The measuring chamber is cleaned by the cleaning gas until the measuring chamber is filled with the cleaning gas. In general, the gas pump is started for 200 s to clean the measuring chamber. The above prepared standard sample gas to be measured and the standard base gas are sampled according to the pre-set injection times, pre-set sample volume of each time and the pre-set interval between two successive injections. In the present embodiment, each sample gas to be measured or standard base gas is divided to 5 parts of 200 ml, and the total volume of the measuring chamber is 700 ml. After each injection, the sampled sample gas is well mixed with the original gas in the measuring chamber. After the fifth times of injection and balancing, the expression of the CO concentration in the measuring chamber is:

$$p_5 = \frac{13682X}{16807} + \frac{3125Y}{16807}.$$

In this embodiment, the standard base gas is measured at first. The standard base gas is divided to 5 parts for injection. After each injection, there is an intermittent time of 19 s before next injection, such that the sampled gas sample can be well mixed with the original gas in the measuring chamber. When the fifth injection is made and the gas in the measuring chamber is fully mixed, the signal level of the standard base gas after the fifth injection is measured and converted into a digital level, and finally the electrical level number of the standard base gas is stored.

Then the gas pump is started for 200 s to clean the measuring chamber, so as to make the measuring chamber full of the cleaning gas. The standard sample gas with a concentration of 1 ppm is divided to 5 parts for injection. When the fifth injection is made and the gas in the measuring chamber is fully mixed, the electrical level number of the standard gas sample of 1 ppm is measured. Finally, based on the electrical level numbers of the above standard gas sample of 1 ppm and of the standard base gas of 0 ppm, an electrical level difference between the standard gas sample of 1 ppm and the standard base gas is calculated. In this embodiment, the electrical level difference is 31, and this data is stored on the computer.

Then the measuring chamber is cleaned again. The signal level of the standard base gas is measured. Then the measuring chamber is cleaned again. After that, the signal level of the standard sample gas of 2 ppm is measured. And an electrical level difference between the standard sample gas of 2 ppm and the standard base gas is calculated. That is after the measurement of each sample to be measured, the measuring chamber is needed to be cleaned again, then the next sample to be measured can be measured. When measuring the electrical level difference between each standard sample gas and the standard base gas, the standard base gas is needed to be measured once again, so as to eliminate the effects of the electrical level zero drift and the cleaning gas. Repeating for several times, the electrical level differences between each standard sample gas and the standard base gas are obtained as follows.

The difference value obtained by subtracting the electrical level number of the standard base gas from the electrical level number of the standard sample gas of 1 ppm is 31.

The difference value obtained by subtracting the electrical level number of the standard base gas from the electrical level number of the standard sample gas of 2 ppm is 61.

The difference value obtained by subtracting the electrical level number of the standard base gas from the electrical level number of the standard sample gas of 3 ppm is 94.

The difference value obtained by subtracting the electrical level number of the standard base gas from the electrical level number of the standard sample gas of 5 ppm is 153.

As shown in FIG. 1, the difference value fitted standard curve obtained by the electrical level differences and the concentration differences between the above each standard sample gas and the standard base gas is as follows:

$$X_S^{CO} - X_B^{CO} = 0.038(D_S^{CO} - D_B^{CO}) - 0.298 \qquad (10).$$

Wherein A is 0.038, B is −0.298. A and B are the fitting constant of the difference value fitted standard curve. $X_S^{CO}$ is CO concentration in the sample gas. $D_S^{CO}$ is CO concentration in the base gas. $D_S^{CO}$ is the electrical level number of the CO in the sample gas. $D_B^{CO}$ is the electrical level number of the CO in the base gas. The linear relationship of the difference value fitted standard curve is good. The reliability of the difference value fitted standard curve (10) is further verified as follows.

The CO standard gas with a concentration of 5 ppm is injected at the sample gas inlet as the sample gas. The ultra-pure nitrogen which is catalyzed and with a low residual CO concentration (≈0 ppm) is injected at the base gas inlet as the base gas. The electrical level difference is measured by the above method. Finally, the electrical level difference between them is 140. The concentration difference is 5.02 ppm according to the difference value fitted standard curve (10). Compared with the actual concentration difference 5 ppm, the difference is little. Therefore, by adopting the "concentration difference/electrical level difference" difference value fitting method, the measurement of the CO concentration difference is accurate and reliable.

The above standard curve (10) is established by the order in which the base gas is measured at first and then the sample gas is measured. In other embodiments, the measurement order of the sample gas and base gas in the measure apparatus can be set conversely. That is the sample gas is measured at first, then the base gas is measured. Then the "concentration difference/electrical level difference" difference value fitted standard curve (10) between the sample gas and the base gas is established. When the sample to be measured in the apparatus is measured in this order, it should be noticed that the order of the measurement of the sample gas and the base gas should be consistent with the order used to establish the difference value fitted standard curve (10).

Part three, application of the difference value fitting method is introduced by taking the collection and measurement of the breath test sample as an example.

Firstly, the sample gas of the subject and the ambient air of the location where the subject is located before the collection of the sample gas are collected respectively. If the CO concentration in the ambient air varies with the location and has a greater volatility, the subject is required to reside 6 hours or more in sampling location before collecting ambient air.

The first measurement after starting the measuring apparatus should be performed for 20 minutes after the start of the measuring apparatus, but the second and subsequent measurements are not subject to this.

A measuring chamber cleaning will be automatically carried out after the start of the measure apparatus.

The sample gas is injected into the sample gas inlet of the apparatus, and the base gas is injected into the base gas inlet.

Then the main measurement interface is presented.

The cleaning gas is used to clean the measuring chamber until the measuring chamber is full of the cleaning gas. Generally, the gas pump is started to clean the measuring chamber for 200 s. The base gas injected into the base gas inlet is measured at first. That is the base gas is divided into 5 parts for injection, and each sample volume is 200 ml. The electrical level number of the CO of the base gas after the fifth injection and balancing is measured and stored. Then the measuring chamber is cleaned again, and the sample gas injected into the sample gas inlet is measured. Similarly, it is divided into 5 parts for injection, and each sample volume is 200 ml. The electrical level number of the sample gas is measured after the fifth injection and balancing in the measuring chamber. Finally, the electrical level difference between the sample gas and the base gas is calculated, and a concentration difference of CO corresponding to the electrical level difference is obtained.

Part four, The compensate principle and compensation formula to calculate and compensate the endogenous CO concentration in exhaled alveolar air by using the CO2 concentration measurement value 1. The relationship of the gas concentration $\rho$, the electrical level number D, the gas concentration measurement value X Under the first measurement condition, the pressure and the temperature are represented as P, $T_{respectively}$, and for the sample whose CO concentration is $\rho$:

$$D = a \cdot \rho + b \quad (11)$$

$$X = A \cdot D + B \quad (12)$$

Wherein formula (11) is a formula for converting the CO concentration into the electrical level number. The electrical level number D measured by the CO sensor is proportional to the CO concentration $\rho$, and wherein the $\rho$ is the real CO volume ratio concentration (V/V) of the sample. The formula (12) is a formula for converting the electrical level number into the concentration measurement value. The concentration measurement value X is proportional to the electrical level number D, and X is the CO volume ratio concentration (V/V) measurement value. If the temperature and the pressure at the measurement time are the same as the temperature and the pressure at the calibration time of the measure apparatus, $\rho = X$, otherwise $\rho \neq X$.

Under the second measurement condition, the pressure and the temperature are represented as P', T' respectively. For the same sample under the second measurement condition, the CO concentration has changed from $\rho$ to $\rho'$. For the same measure apparatus (a, b, A, B remain unchanged), the same sample is measured, and there is:

$$D \rightarrow D' D' = a \cdot \rho' + b \quad (13)$$

$$X \rightarrow X' X' = A \cdot D' + B \quad (14)$$

2. Determination of the relationship between X' and X
Substituting (13) into (14) and there is $$X' = A(a \cdot \rho' + b) + B = A \cdot a \cdot \rho' + (A \cdot b + B) \quad (15)$$

Substituting (11) into (12) and there is $$X = A(a \cdot \rho + b) + B = A \cdot a \cdot \rho + (A \cdot b + B) \quad (16)$$

According to the ideal gas equation (assuming the ideal gas), there is $$\rho' = \rho \frac{TP'}{T'P} \quad (17)$$

Substituting (17) into (15) and there is $$X' = a \cdot A \cdot \rho \frac{TP'}{T'P} + (A \cdot b + B) \quad (18)$$

From (16) and (18), there is $$\frac{X' - (A \cdot b + B)}{X - (A \cdot b + B)} = \frac{TP'}{T'P} \quad (19)$$

That is $$X = \frac{TP'}{T'P} X' + \left[(A \cdot b + B)\left(1 - \frac{T'P}{TP'}\right)\right] \quad (20)$$

As during the actual measurement, the interference of the base gas on the measurement results is needed to be removed, and the measuring conditions of sample gas and the bas gas are the same, so, $$X_S = \frac{TP'}{T'P} X'_S + \left[(A \cdot b + B)\left(1 - \frac{T'P}{TP'}\right)\right] \quad (21)$$

$$X_B = \frac{TP'}{T'P} X'_B + \left[(A \cdot b + B)\left(1 - \frac{T'P}{TP'}\right)\right] \quad (22)$$

Hence $$X_S - X_B = \frac{T'P}{TP'}(X'_S - X'_B) \quad (23)$$

In order to simplify the formula and the calculation process, a constant C is set to be, $$c = \frac{T'P}{TP'}. \quad (24)$$

3. The endogenous CO concentration in exhaled alveolar air is calculated and compensated by the $CO_2$ concentration measurement value.

The formula (23) is suitable to the measurement of CO and $CO_2$. Wherein, d is set to be the proportion of alveolar gas in the whole sample, and M is set to be the endogenous CO concentration in exhaled alveolar air. $CO_2$ in the exhaled alveolar air is 5%, then $$d = \frac{X_S^{CO_2} - X_B^{CO_2}}{5\%} \quad (25)$$

$$d = \frac{X_S^{CO} - X_B^{CO}}{M} \quad (26)$$

From the formulas (25) and (26), we can see:

$$M = \frac{X_S^{CO} - X_B^{CO}}{d}, \left(\text{wherein}, d = \frac{X_S^{CO_2} - X_B^{CO_2}}{5\%}\right). \quad (27)$$

From the formula (27) we can see that, the CO concentration is compensated and corrected by the relatively stable $CO_2$ concentration in the exhaled alveolar air, and then the problem that there is a difference between the measurement values and the actual values caused by the different temperatures and pressures can be eliminated. Meanwhile, through the proportional concentration or dilution relationship between the $CO_2$ concentration and the CO, the formula (27) can be used to eliminate the deviation of the measured value due to the mixing of the ambient gas caused by the inconsistent operation during the exhaled alveolar gas sampling and injecting.

The present application proposes a compensation method which uses the concentration measurement value of one component to compensate the concentration measurement value of another component in the concentration measurement of multi-component gas mixtures (Under certain conditions, the measured value is different from the real value, by the present compensation method, it is convenient to make the compensated measured value equal to the true value after the compensation). The compensation method is suitable for the condition in which the concentration measurement is performed by gas absorption spectroscopy and the measuring chamber is communicated with external environment through the exhaust port. In the present application, this compensation method is specifically applied to the calculation and the compensation of the endogenous CO measurement value in exhaled alveolar air. Specifically, the measured $CO_2$ concentration difference between the sample gas and the base gas, are used to calculate the volume ratio (V/V) concentration net value M of the endogenous CO in exhaled alveolar air via the compensation formula.

Part Five, Examples of Application of Compensation Formula

A first preferred embodiment of compensating and correcting the CO concentration by using compensation formula (27), comprises following steps.

S10. Under the same temperature and pressure, the $CO_2$ concentration $X_S^{CO_2}$, $X_B^{CO_2}$ or the concentration difference $(X_S^{CO_2}-X_B^{CO_2})$ in the sample gas and the base gas are measured. The CO concentration $X_S^{CO}$, $X_B^{CO}$ or the concentration difference $(X_S^{CO}-X_B^{CO})$ in the sample gas and the base gas are also measured. The pressure and temperature P, T of the first measurement condition described above are the pressure and temperature of the measuring apparatus at the calibration time, however the pressure and temperature P', T' of the second measurement condition are the pressure and temperature of the sample at the measurement time.

S20. The formula (27) is used to calculate the volume ratio (V/V) concentration net value M of the endogenous CO in exhaled alveolar air.

In the second embodiment of compensating and correcting the CO concentration by using compensation formula (27), based on the first preferred embodiment, a step is further comprised before step S20:

S15. The formula (25) is used to calculate the proportion of alveolar gas in the whole sample for make following determination.

If d falls into the range of [0.6,1.5], it indicates that the ratio is within the normal correctable range, the process proceeds directly to step S20 to use formula (27) to calculate the volume ratio (V/V) concentration net value M of the endogenous CO in exhaled alveolar air.

If d falls out of the range of [0.6, 1.5], it indicates that there are serious errors during the sample gas collection or intake process, the correction error is too large and re-injection and re-determination are needed.

In the method of measuring the endogenous CO concentration in exhaled alveolar air according to the third preferred embodiment of the present application, based on the first preferred embodiment, a step is further comprised before step S20.

S16. If d falls into the range of [0.6,1.5], it is also necessary to further determine whether the d value falls into the fluctuation range of the d value that may be caused by individual differences in $CO_2$ concentrations in the alveolar gas of the subjects. If the d value falls into the fluctuation range of the d value that may be caused by the individual differences in the endogenous $CO_2$ concentration of the alveolar gas in the subject, for example, [1, 1.1], it is considered that the $CO_2$ concentration difference between the sample gas and the base gas deviating from 5% is due to the individual differences in the concentration of endogenous $CO_2$ in the alveolar gas of the subject, and it is not considered to be caused by the inconsistency of the operation method of gas production and/or intake. Therefore, it is directly determined that d=1. Then the process goes to step S20. At this time, the volume ratio (V/V) concentration net value M of the endogenous CO in the exhaled alveolar air is calculated by the following formula:

$$M=X_S^{CO}-X_B^{CO}.$$

If d falls out of the range of [1, 1.1], the process goes directly to step S20.

In the method of measuring the endogenous CO concentration in exhaled alveolar air according to another preferred embodiment of the present application, before measuring the CO concentration in the sample gas and the base gas, the water vapor and $CO_2$ should be removed from the sample gas and the base gas. The present application uses the CO probe and the $CO_2$ probe to measure the CO concentration and the $CO_2$ concentration. For example, the CO probe uses a high sensitivity InSb infrared detector to meet CO detection index. The $CO_2$ probe uses a NDIR probe with wide temperature compensation, a good stability, anti-water gas interference and high precision. The elimination of the background noise in the CO detection is mainly completed through a difference calculation between the sample gas measurement results and the base gas measurement results (that is the "difference value fitting method"). Because the background noise contained in the sample gas and the base gas during the measurement period is basically the same. At the same time, a separate $CO_2$ measuring chamber in the present application was used to measure the $CO_2$ concentration alone and to avoid the effect of gas flow on the measurement results. After using the cleaning gas to blow out the residual gas in the $CO_2$ measuring chamber before each measurement, the sample gas which is 100 times larger than the volume of the $CO_2$ chamber is delivered into the $CO_2$ measuring chamber to ensure that the gas inside the $CO_2$ chamber is completely the sample gas. It will be measured after the gas is balanced (such as 30 s).

Part Six, Example of the Apparatus for Measuring the Endogenous CO concentration in exhaled alveolar air In order to achieve the purposes of injection in small volumes, multiple times and intermittently, and results compensation and correction, the present application designs an apparatus for measuring endogenous CO concentration in exhaled alveolar air. In particular, the cylinder is used for injection. Through the motion of the cylinder piston, the gas in the gas bag will be pumped into the cylinder, and then injected into the measuring chamber assembly.

Figure 2:
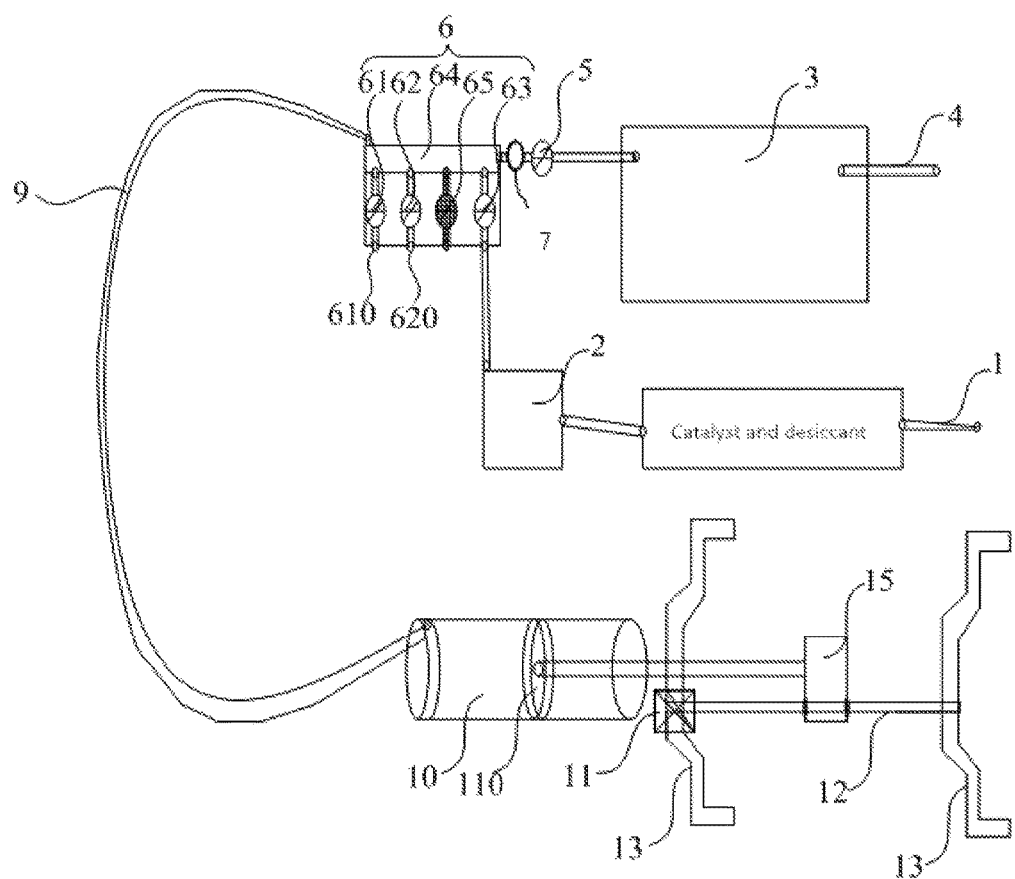
FIG. 2 is a structure diagram of the injecting-sample-into-chamber system, according to a preferred embodiment of the present application.

FIG. 2 shows the structure of the injecting-sample-into-chamber system of the apparatus for measuring endogenous CO concentration in exhaled alveolar air, according to a preferred embodiment of the present application. As shown in FIG. 2, the injecting-sample-into-chamber system mainly comprises a gas inlet 1, a gas pump 2, a measuring chamber assembly 3, an exhaust port 4, a general solenoid valve 5, a gas pipe 9, a cylinder 10, an absorption bag assembly 7, a gas control unit 6 and a driving unit (not shown). Wherein, the gas inlet 1 is connected with the gas pump 2 which is connected with the measuring chamber assembly 3 through the general solenoid valve 5. The exhaust port 4 is disposed on the measuring chamber assembly 3. One end of the gas pipe 9 is connected with the gas control unit 6, and the other end of which is connected with the cylinder 10 which is further connected with the driving unit used to drive the reciprocating motion of the cylinder 10. A piston 110 is disposed inside the cylinder body of the cylinder 10, and before the gas to be measured is injected into the measuring chamber assembly 3 through the movement of the piston 110, the absorption bag assembly is used to absorb $CO_2$ and water vapor.

The gas control unit 6 comprises a gas passage switching buffer 64, a sample gas solenoid valve 61, a base gas solenoid valve 62, and a gas pump solenoid valve 63. The gas passage switching buffer 64 is connected between the gas pipe 9 and the general solenoid valve 5, while the sample gas solenoid valve 61, the base gas solenoid valve 62 and the gas pump solenoid valve 63 are all connected into the gas passage switching buffer 64. The gas passage switching buffer 64 is communicated with the general solenoid valve 5 for delivering the gas into the measuring chamber assembly 3. A sample gas inlet 610 disposed on the sample gas solenoid valve 61 is connected with the sample gas bag for delivering the sample gas into the gas passage switching buffer 64. A base gas inlet 620 disposed on the base gas solenoid valve 62 is connected with the base gas bag for delivering the base gas into the gas passage switching buffer 64. The gas pump solenoid valve 63 is connected with the gas pump 2 for delivering the cleaning gas into the gas passage switching buffer 64. In other embodiments, the gas control unit 6 further comprises a spare solenoid valve 65. When one of the sample gas solenoid valve 61, the base gas solenoid valve 62 or the gas pump solenoid valve 63 is damaged, it can be used for replacement, or for future expansion.

The driving unit is connected with the cylinder 10 for powering the movement of the cylinder 10. The driving unit comprises a base 13, a rotating screw rod 12, a stepping motor 11 and a slider 15.

There are two bases 13 of exactly the same size. The two ends of the rotating screw rod 12 are fixedly connected with the two bases 13. The stepping motor 11 is disposed on one of the bases 13. The slider 15 is disposed on the rotating screw rod 12. The slider 15 is connected with the piston of the cylinder. Specifically, in the present embodiment, the stepping motor 11 drives the rotating screw rod 12 to rotate so as to drive the slider 15. Since the slider 15 is connected with the cylinder 10, the slider 15 will drive the cylinder 10 to move so as to inject the gas to be measured into the measuring chamber assembly 3.

The working process of the injecting-sample-into-chamber system is as follows.

(1) Clean Measuring Chamber

The sample gas is injected into the sample gas inlet 610 of the sample gas solenoid valve 61. The base gas is injected into the base gas inlet 620 of the base gas solenoid valve 62. After the instrument measurement procedure is started, the sample gas solenoid valve 61 and the base gas solenoid valve 62 are turned off, and the gas pump solenoid valve 63 and the general solenoid valve 5 are turned on. The gas pump 2 starts to work. The cleaning gas (air) entered from the gas inlet 1 goes into the measuring chamber assembly 3 after being processed by a desiccant and a CO catalyst, and then is exhausted through the exhaust port 4. Then a clean of 200 s will be performed.

(2) Measurement of the Base Gas

After the cavity of the measuring chamber assembly 3 is cleaned, the sample gas solenoid valve 61, the gas pump solenoid valve 63 and the general solenoid valve 5 are turned off, and the base gas solenoid valve 62 is turned on. The stepping motor 11 drives the rotating screw rod 12 to rotate. The cylinder piston 110 is moved from the leftmost end to the rightmost end by the slider 15. After a certain amount (such as 200 ml) of the base gas is taken, the solenoid valves are switched. The sample gas solenoid valve 61, the base gas solenoid valve 62 and the gas pump solenoid valve 63 are turned off, and the general solenoid valve 5 is turned on. After the base gas enters into the absorption package assembly through the cylinder 10 to clean the $CO_2$ and water vapor, the base gas is injected into the measuring chamber assembly 3 (the cylinder piston 110 is moved from the rightmost end to the leftmost end by the slider 15). The cylinder 10 is subjected to five consecutive pumping processes. A total of 1000 ml base gas is delivered into the measuring chamber assembly 3. Then the base gas is measured.

(3) Measurement of the Sample Gas

After the measurement of the base gas, the step (1) is repeated to clean the cavity of measuring chamber assembly 3. After a clean of 200 s, the solenoid valves are switched. The base gas solenoid valve 62, the gas pump solenoid valve 63 and the general solenoid valve 5 are turned off, and the sample gas solenoid valve 61 is turned on. The stepping motor 11 drives the rotating screw rod 12 to rotate. The cylinder piston 110 is moved from the leftmost end to the rightmost end by the slider 15. After a certain amount (such as 200 ml) of the sample gas is taken, the solenoid valves are switched. The sample gas solenoid valve 61, the base gas solenoid valve 62 and the gas pump solenoid valve 63 are turned off, and the general solenoid valve 5 is turned on. After the sample gas enters into the absorption package assembly through the cylinder 10 to clean the $CO_2$ and water vapor, the sample gas is delivered into the measuring chamber assembly 3 (the cylinder piston 110 is moved from the rightmost end to the leftmost end by the slider 15). After the sample gas enters into the measuring chamber assembly 3, the measurement is started. The cylinder 10 starts to continue pumping the sample gas, for example, the sample gas is divided into 5 parts for injection 5 times, and each time 200 ml gas are sampled. At first, 200 ml sample gas is injected, and then four injections are implemented. Finally, a total amount of 1000 ml sample gas is delivered into the measuring chamber assembly. Then the sample gas is measured.

The test system of the apparatus for measuring CO concentration in the exhaled alveolar air of the present application comprises a tracheal line, a $CO_2$ measuring chamber, a CO measuring chamber, a processing unit. The $CO_2$ measuring chamber and the CO measuring chamber are disposed inside the measuring chamber assembly 3, and connected to the gas inlet through the tracheal line. The $CO_2$ measuring chamber and the CO measuring chamber are connected to the processing unit respectively, for measuring the $CO_2$ concentration $X_S^{CO_2}$, $X_B^{CO_2}$ or the concentration difference $(X_S^{CO_2}-X_B^{CO_2})$ of the sample gas and the base gas, the CO concentration $X_S^{CO}$, $X_B^{CO}$ or the concentration difference $(X_S^{CO}-X_B^{CO})$ of the sample gas and the base gas under the same temperature and pressure. The processing unit obtains the above measurement values or the difference value between the above sample gas measurement value and the base gas measurement value, and uses formula (27) to calculate the volume ratio (V/V) concentration net value M of the endogenous CO in exhaled alveolar air.

The absorption package assembly of the present measure apparatus can be fixedly or detachably mounted between the gas inlet and the CO measuring chamber through the connection of the tracheal line. It can be replaced easily and immediately after the absorber inside the absorption package assembly has failed.

While the embodiments of the present application have been described with reference to the accompanying drawings, the application is not limited to the specific embodiments described above, and the specific embodiments described above are merely illustrative and not restrictive. It will be apparent to those skilled in the art that various changes may be made therein without departing from the scope of the application as defined by the appended claims and the claims which come within the meaning of the application.

The invention claimed is:

1. A method for measuring an endogenous CO concentration in alveolar air, comprising following steps:
   S1. setting an injecting-sample-into-chamber mode for sample gas and base gas of a set of breath test samples in absorption spectroscopy; wherein the sample-injected-into-chamber mode comprises injection times of the sample gas and the base gas, a volume of each injection, an interval between two successive injections;
   S2. establishing a "concentration difference/electrical level difference" difference value fitted standard curve for the CO and the $CO_2$ respectively, by using standard sample gas and standard base gas with known concentrations of CO and $CO_2$;
   S3. measuring electrical level number corresponding to the concentration of the sample gas and the base gas at a same temperature and pressure by a same apparatus and calculating an electrical level difference and obtaining a concentration difference of the CO and a concentration difference of the $CO_2$ based on the difference value fitted standard curve in S2;
   S4. calculating a concentration M in a volume ratio (V/V) of the endogenous CO in the alveolar air according to following compensation formula:

$$M = \frac{X_S^{CO} - X_B^{CO}}{d},$$

wherein, $d = \frac{X_S^{CO_2} - X_B^{CO_2}}{5\%}$.

2. The method for measuring an endogenous CO concentration in alveolar air according to claim 1, wherein, in the step S1, the injecting-sample-into-chamber mode comprises per injection volume of 40 ml~400 ml, an injection speed of 10 ml/s~200 ml/s, 2-9 injection times of each sample gas and each base gas, and the interval between two successive injections of 12 s~48 s.

3. The method for measuring an endogenous CO concentration in alveolar air according to claim 2, wherein before measuring the CO gas in the sample gas and the base gas, water vapor and $CO_2$ gas are removed from the sample gas and the base gas.

4. The method for measuring an endogenous CO concentration in alveolar air according to claim 1, wherein the step S2 specifically comprises the following steps:
   S201. preparing CO standard sample gas of different concentrations and one standard base gas;
   S202. taking gas treated by CO catalyst and desiccant or other catalytic or drying processes as cleaning gas to clean measuring chamber until the measuring chamber is filled with the cleaning gas;
   S203. according to the above injecting-sample-into-chamber mode, measuring electrical level numbers of the standard sample gas and the standard base gas respectively; according to the above electrical level numbers of the standard sample gas and the standard base gas, obtaining the electrical level difference between the standard sample gas and the standard base gas;
   S204. according to the electrical level difference and the concentration difference between the standard sample gas and the standard base gas, fitting the "concentration difference/electrical level difference" difference value fitted standard curve with following expression:

$$X_S^{CO} - X_B^{CO} = A(D_S^{CO} - D_B^{CO}) + B;$$

wherein, A and B are fitted constants, $X_S^{CO}$ is the CO concentration in the sample gas, $X_B^{CO}$ is the CO concentration in the base gas, $D_S^{CO}$ is corresponding electrical level number of the CO concentration in the sample gas, $D_B^{CO}$ is corresponding electrical level number of the CO concentration in the base gas.

5. The method for measuring an endogenous CO concentration in alveolar air according to claim 4, wherein before measuring the CO gas in the sample gas and the base gas, water vapor and $CO_2$ gas are removed from the sample gas and the base gas.

6. The method for measuring an endogenous CO concentration in alveolar air according to claim 4, wherein, the step S203 further comprises:
   cleaning the measuring chamber by the cleaning gas until the measuring chamber is filled with the cleaning gas;
   according to the injecting-sample-into-chamber mode, injecting the standard base gas into the measuring chamber to obtain and store the electrical level number of the standard base gas after final injection and balancing;
   cleaning the measuring chamber by the cleaning gas until the measuring chamber is filled with the cleaning gas;
   according to the injecting-sample-into-chamber mode, injecting a first standard sample gas into the measuring chamber to obtain and store the electrical level number of the first standard sample gas after final injection and balancing;
   obtaining the electrical level difference between the first standard sample gas and the standard base gas according to the electrical level numbers of the first standard sample gas and the standard base gas;
   cleaning the measuring chamber by the cleaning gas until the measuring chamber is filled with the cleaning gas;
   according to the injecting-sample-into-chamber mode, injecting the standard base gas into the measuring chamber to obtain and store the electrical level number of the standard base gas after final injection and balancing;
   cleaning the measuring chamber by the cleaning gas until the measuring chamber is filled with the cleaning gas;
   according to the injecting-sample-into-chamber mode, injecting a second standard sample gas into the measuring chamber to obtain and store the electrical level number of the second standard sample gas after final injection and balancing;

obtaining the electrical level difference between the second standard sample gas and the standard base gas according to the electrical level numbers of the second standard sample gas and the standard base gas;

repeating the above procedure to obtain a group of "concentration difference/electrical level difference" data pairs of a group of the standard sample gas and the standard base gas pairs.

7. The method for measuring an endogenous CO concentration in alveolar air according to claim 6, wherein before measuring the CO gas in the sample gas and the base gas, water vapor and $CO_2$ gas are removed from the sample gas and the base gas.

8. The method for measuring an endogenous CO concentration in alveolar air according to claim 1, wherein in the step S3, when measuring the concentration difference between the sample gas and the base gas in a set of breath test samples, its injecting order is the same as that of the standard sample gas and the standard base gas when fitting the difference value fitted standard curve.

9. The method for measuring an endogenous CO concentration in alveolar air according to claim 8, wherein before measuring the CO gas in the sample gas and the base gas, water vapor and $CO_2$ gas are removed from the sample gas and the base gas.

10. The method for measuring an endogenous CO concentration in alveolar air according to claim 1, wherein before measuring the CO gas in the sample gas and the base gas, water vapor and $CO_2$ gas are removed from the sample gas and the base gas.

11. An apparatus for measuring an endogenous CO concentration in alveolar air, being capable of measuring both CO concentration and $CO_2$ concentration and comprising:

a $CO_2$ gas measuring chamber and a CO gas measuring chamber, wherein the $CO_2$ gas measuring chamber and the CO gas measuring chamber are connected with a gas inlet through a tracheal line; wherein concentration of $CO_2$ gas $X_S^{CO_2}$, $X_B^{CO_2}$ or concentration difference of $CO_2$ gas ($X_S^{CO_2} - X_B^{CO_2}$) in sample gas and base gas, as well as concentration of CO gas $X_S^{CO}$, $X_B^{CO}$ or concentration difference of CO gas ($X_S^{CO} - X_B^{CO}$) in the sample gas and the base gas are measured at the same temperature and pressure;

a processing unit, used for calculating a concentration net value M in a volume ratio (V/V) of the endogenous CO in exhaled alveolar air according to following compensation formula:

$$M = \frac{X_S^{CO} - X_B^{CO}}{d},$$

wherein, $d = \frac{X_S^{CO_2} - X_B^{CO_2}}{5\%}$.

12. The apparatus for measuring an endogenous CO concentration in alveolar air according to claim 11, wherein further comprises an injecting-sample-into-chamber system comprising the gas inlet, a gas pump, a general solenoid valve, a measuring chamber and an exhaust port; wherein the gas inlet is connected with the gas pump which is further connected with the measuring chamber through the general solenoid valve, the exhaust port is disposed on the measuring chamber which is communicated with external environment through the exhaust port; wherein, the injecting-sample-into-chamber system further comprises a gas control unit, a gas pipe and a cylinder; the gas control unit comprises a gas passage switching buffer, a sample gas solenoid valve, a base gas solenoid valve and a gas pump solenoid valve; wherein the gas passage switching buffer is connected between the gas pipe and the general solenoid valve; the sample gas solenoid valve, the base gas solenoid valve and the gas pump solenoid valve are all connected into the gas passage switching buffer; the sample gas solenoid valve and the base gas solenoid valve are respectively used for delivering the sample gas and the base gas to the gas passage switching buffer; the gas pump solenoid valve connected with the gas pump is used for delivering cleaning gas to the gas passage switching buffer; the cylinder connected with the gas pipe is used for injecting either the sample gas or the base gas to be measured into the measuring chamber through the gas pipe.

13. The apparatus for measuring an endogenous CO concentration in alveolar air according to claim 12, wherein the gas control unit further comprises a spare solenoid valve for replacing the sample gas solenoid valve, the base gas solenoid valve or the gas pump solenoid valve.

14. The apparatus for measuring an endogenous CO concentration in alveolar air according to claim 12, wherein, the injecting-sample-into-chamber system further comprises a driving unit connected with a piston of the cylinder; wherein the driving unit comprises a base, a rotating screw rod and a stepping motor which are fixed on the base, and a slider which is disposed on the rotating screw rod and connected with the cylinder; the stepping motor drives the rotating screw rod to rotate so as to drive the piston to move, and inject either the sample gas or the base gas to be measured into the measuring chamber through the gas pipe.

* * * * *